US011427326B2

(12) United States Patent
Faizan et al.

(10) Patent No.: US 11,427,326 B2
(45) Date of Patent: Aug. 30, 2022

(54) AUTOMATED AIRCRAFT TRAY TABLE DISINFECTING SYSTEM USING ULTRA-VIOLET LIGHT

(71) Applicant: Mirza Faizan, Irving, TX (US)

(72) Inventors: Mirza Faizan, Irving, TX (US); Yumna Syeda Ali Shah, Murphy, TX (US); Nimra Syeda Ali Shah, Murphy, TX (US); Bilal Syed Ali Shah, Murphy, TX (US)

( * ) Notice: Subject to any disclaimer, the term of this patent is extended or adjusted under 35 U.S.C. 154(b) by 0 days.

(21) Appl. No.: 17/185,008

(22) Filed: Feb. 25, 2021

(65) Prior Publication Data

US 2021/0269158 A1 Sep. 2, 2021

Related U.S. Application Data

(60) Provisional application No. 62/982,245, filed on Feb. 27, 2020.

(51) Int. Cl.
*B64D 11/06* (2006.01)
*A61L 2/00* (2006.01)

(52) U.S. Cl.
CPC ........ *B64D 11/0638* (2014.12); *A61L 2/0047* (2013.01)

(58) Field of Classification Search
CPC ...... A47C 7/70; B64D 11/0638; B60N 3/004; A61L 2/0047
USPC ........................................................ 297/146
See application file for complete search history.

(56) References Cited

U.S. PATENT DOCUMENTS

| | | | | |
|---|---|---|---|---|
| 9,701,409 B2* | 7/2017 | Valdes | ............... | B60N 3/004 |
| 10,301,806 B2* | 5/2019 | Childress | .............. | A61L 2/10 |
| 10,702,618 B2* | 7/2020 | Callahan | .............. | A61L 2/26 |
| 10,933,821 B2* | 3/2021 | Line | .......... | A61L 2/10 |
| 11,007,292 B1* | 5/2021 | Grenon | ............... | F21V 11/08 |
| 2016/0250362 A1* | 9/2016 | Mackin | ............... | B64D 11/06 |
| | | | | 244/118.5 |
| 2017/0290935 A1* | 10/2017 | Boodaghians | ............ | A47L 9/02 |
| 2018/0064833 A1* | 3/2018 | Childress | .............. | A61L 2/10 |
| 2018/0209613 A1* | 7/2018 | Callahan | .............. | B64D 11/02 |
| 2021/0286412 A1* | 9/2021 | Lin | .......... | A61L 2/0047 |
| 2021/0323678 A1* | 10/2021 | Kohlmeier-Beckmann | ................ | |
| | | | | B64D 11/0638 |
| 2021/0353809 A1* | 11/2021 | Ou Yang | ................ | A61L 2/28 |
| 2021/0363361 A1* | 11/2021 | Poteet | ............ | B60N 2/75 |
| 2021/0379217 A1* | 12/2021 | Beckman | ............... | A61L 2/24 |
| 2021/0393823 A1* | 12/2021 | Childress | .............. | A61L 9/20 |
| 2022/0008583 A1* | 1/2022 | Garcia | ............ | A61L 2/26 |
| 2022/0023468 A1* | 1/2022 | Sears | ............ | A61L 2/10 |
| 2022/0031876 A1* | 2/2022 | Ubale | ............ | A61L 2/10 |

FOREIGN PATENT DOCUMENTS

EP        3287146 A1 *  2/2018  .............. A61L 2/10
WO   WO-2021214574 A1 * 10/2021

* cited by examiner

*Primary Examiner* — Jose V Chen

(57) ABSTRACT

A sanitation assembly attaches over a surface inside a tray table of an aircraft. A source of UV radiation is mounted to the assembly and configured to direct UVC radiation to the tray table at a predetermined dosage, wherein the assembly uses for disinfection of the aircraft tray table. The embodiments may use UV light sources and/or a disinfection unit powered by a fuel cell or other external power source.

8 Claims, 4 Drawing Sheets

AUTOMATED AIRCRAFT TRAY TABLE DISINFECTING SYSTEM USING ULTRA-VIOLET LIGHT

TECHNICAL FIELD

The present invention relates generally to an aircraft tray table, and more specifically to a system to disinfect aircraft tray table automatically for keeping passengers safe from pathogens, microbes, wherein the system uses UVC LIGHT from a removable and rechargeable power source.

BACKGROUND OF THE INVENTION

Every year millions of passengers take an airplane to travel without knowing that they touch, sit and eat on surfaces that are up to 50 times more infected than a toilet seat. Infectious disease transmission among air travelers is a significant private and public health concern. Commonly serious viral(Influenza), Bacterial and Fungal pathogens are spread from mutual contacted surfaces. In a test conducted in a study, it was found that the toilet seat of an airport scored 35 on a germ-meter test whereas the aircraft tray table scored 1688 meaning it is almost 50 times more infected than a toilet seat. Said tray tables are found to have different types of bacteria which can cause serious illness to humans. Every time an airplane lands, the cabin crew is busy preparing for 'turnaround', thus sending the plane back in the air to make their money. They do not have ample time to thoroughly clean and disinfect the plane.

When a new passenger occupies an airplane seat, the passenger might be getting a seat occupied by someone who is infected with a deadly virus or bacteria and may have used the tray table to eat food. These infected tray tables are the major cause for the spread of disease during air travel.

There have been attempts to sanitize various parts of an aircraft like lavatory, cabin, washbasin, etc. However, currently, there is no system in place to automatically sanitize the tray table, which is the most infected and most used surface by a passenger during travel.

This is probably because the tray table is to be closed by the passenger to exit from their seat at their destination. Airline crew and their cleaning personnel need to open each tray table, disinfect and then close, thus requiring a lot of time. Fastest disinfectant though UVC is effective germicidal technology not only for air but also for surfaces.

However, there is no currently available technology to effectively and efficiently disinfectant the aircraft surface. It takes a minimum of 18 to 20 seconds to disinfect each tray table. Chemical disinfectant is labor-intensive with potential harmful residues. For an average aircraft with 300 seats, it will take approximately 2 hours to just disinfect all tray tables. Airlines do not have this much time and therefore they silently neglect leaving passengers at the mercy of viruses, bacteria, and germs.

| Title | Pat. No. | Country |
|---|---|---|
| Uv-c sterilizer | EP2174670B1 | European Patent Office |
| Method for disinfecting an aircraft cabin using a lighting assembly and a lighting assembly therefor | WO2019068189A1 | WIPO (PCT) |
| Systems and methods for treatment of cabin surfaces and air | US9907870B2 | US |
| Aircraft galley and lavatory | US20140059796A1 | US |

-continued

| Title | Pat. No. | Country |
|---|---|---|
| disinfection appliance, aircraft, and method for disinfecting a washbasin | BR102015031381A2 | Brazil |
| Automatic UV wagon to sanitize aircraft | JP6439253B2 | Japan |
| Sanitizing surfaces associated with aircraft areas | US10406253B2 | US |
| Ultraviolet autonomous trolley for sanitizing aircraft | US8999238B2 | US |

All of these conventionally available method/system or a computer program product, and some other method/system presently known in the art have had some flaws in design or mechanism and lacks precision. Most of the existing devices are too expensive and time consuming to be practical for most users. Some shortfalls of the existing method/system or a computer program product include manual interference. In light of this, there is a need for a method/system or a computer program product that overcomes these constraints.

In the light of these facts, it is of great advantage to the safety of the passengers that there is a system to kill the microbes using a disinfectant. Furthermore, if a system using the UVC light kills the pathogens, it will save hundreds of lives worldwide. There is a need for an automatic sanitizing system that is designed to kill the microbes, pathogens using the UVC light.

None of the above inventions and patents, taken either singly or in combination, is seen to describe the present invention as claimed. Thus, an automated aircraft tray table disinfectant system solving the aforementioned problems is desired.

Features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed. The present invention addresses the issues as discussed above.

SUMMARY OF THE INVENTION

The present invention addresses one or more of the deficiencies with respect to the prior art.

In one illustrative embodiment, an apparatus comprises a disinfection system for disinfecting aircraft tray table and an activation system. The disinfection system emits ultraviolet radiation to perform a disinfection process inside a tray table of the aircraft when the tray table is not in use. The disinfection system is inactive when the tray table is in use. The activation system controls the activation and deactivation of the disinfection system.

In another illustrative embodiment, the method for disinfecting the tray table is provided. A determination is made as to whether a set of criteria for activation of a disinfection system that emits-ultraviolet radiation to perform a disinfection process inside a tray table, has been met. In response to a determination that the set of criteria has been met, the disinfection system is activated, to perform the disinfection process inside the tray table, using the UVC radiation.

The present disclosure generally relates to a system for disinfecting aircraft tray table. The device includes a sanitizing assembly coupled to a tray table, wherein the system includes a removable and rechargeable power source of UVC radiation. The power source can be recharged by a USB port located at the back portion of the aircraft seat or drawing power from the In-Flight Entertainment System installed on an airplane seat.

The embodiments may use UVC light sources and/or a disinfection unit powered by a fuel cell or other external power source.

According to an object of the present invention, the power source of UVC radiation is configured to direct UVC radiation to the surface at a dosage sufficient to diminish microbial loads to acceptable levels. The current disclosure provides a rapid, safe, and effective means of disinfecting the tray table by exposure to germicidal UV-C light. The power source is configured to emit the UV light onto the tray table when the tray table is secured in an upright positioni.e when the safety switch is closed and prevents the UV light source from emitting the UV light when the tray table is not secured in the upright position. The tray table position a sensor, wherein the sensor may be configured to detect when the tray table is secured in the upright position after the switches are closed and an array of UV-C sensors scan the tray table.

An object of the present invention, the system may include a master control unit remotely located from and in communication with the disinfection system for disinfecting the aircraft tray table of the plurality of seat assemblies.

According to an embodiment of the present invention, the UV light source may include one or more light-emitting diodes, Still further, one embodiment of the ultraviolet light source may include a plurality of ultraviolet light generators, wherein the ultraviolet light generators may be LEDs. The sanitation assembly includes laminar surfaces that are configured to reflect the UV light emitted from the UV light source onto surfaces of the tray table. A light sealant may be used on the edges of the tray table so that the UV radiations are not emitted outside from the tray table. In one embodiment, the sanitation assembly is securely connected to a seat assembly. For example, the sanitation assembly may be secured to a back portion of the seat assembly. The system may also include a microprocessor in communication with the sanitation control unit. The microprocessor may be configured to monitor and control the operation of the sanitation assembly for the tray table.

According to another object of the present invention, the system further includes a sensor system configured to monitor the power source associated with the operation of the switches. The sanitation assembly includes one or more reflective surfaces that are configured to reflect the UV light emitted from the UV light source onto surfaces of the tray table. In the extreme case of a bioterror threat of dispersing particularly lethal microbes via aircraft, this disclosure has the potential of preventing mass casualties.

Other objects, advantages, and features of this invention will become more apparent from the following description.

The details of one or more implementations are set forth in the accompanying description below. Other aspects, features, and advantages of the subject matter disclosed herein will be apparent from the description and the claims.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

Features, elements, and aspects of the invention that are referenced by the same numerals in different figures represent the same, equivalent, or similar features, elements, or aspects in accordance with one or more embodiments.

Figure 1:
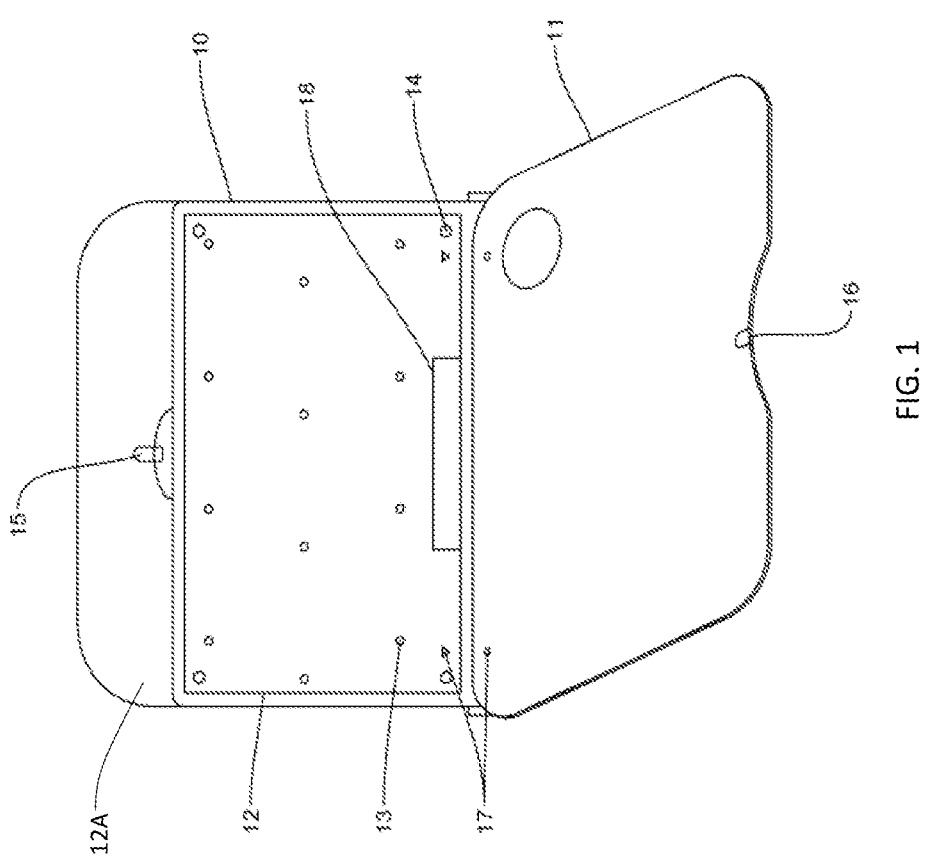

The following figure depicts a certain illustrative embodiment of the invention. This depicted embodiment is to be understood as illustrative of the invention and not as limiting in any way.

Figure 2:
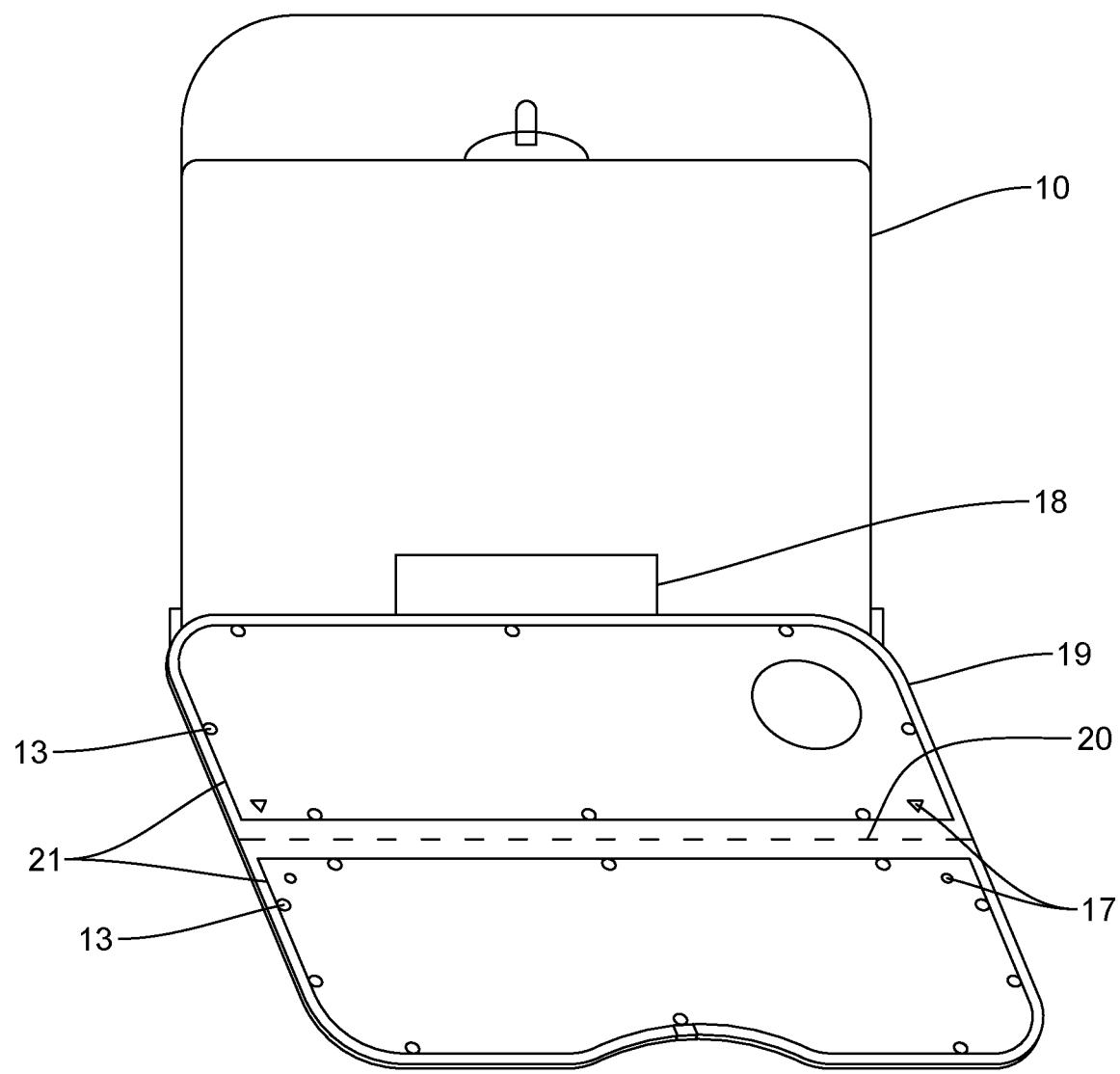
Figure 3:
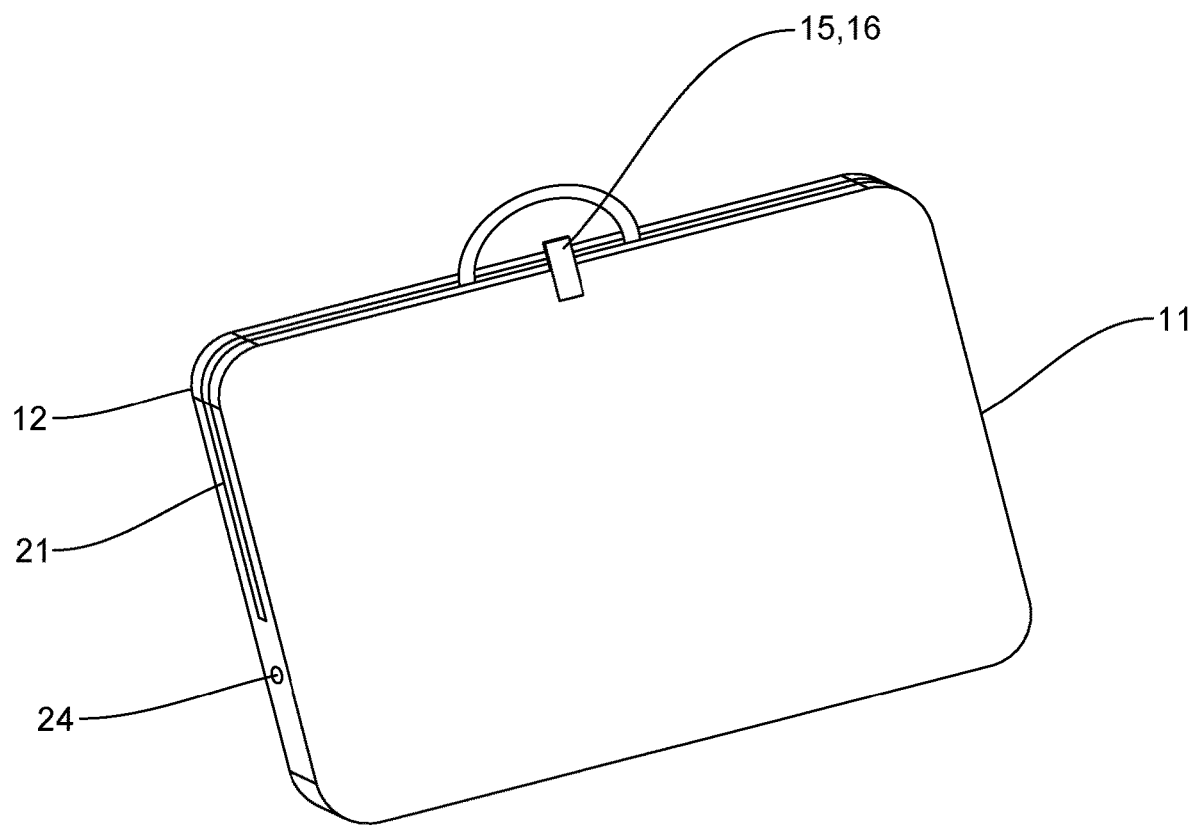
Figure 4:
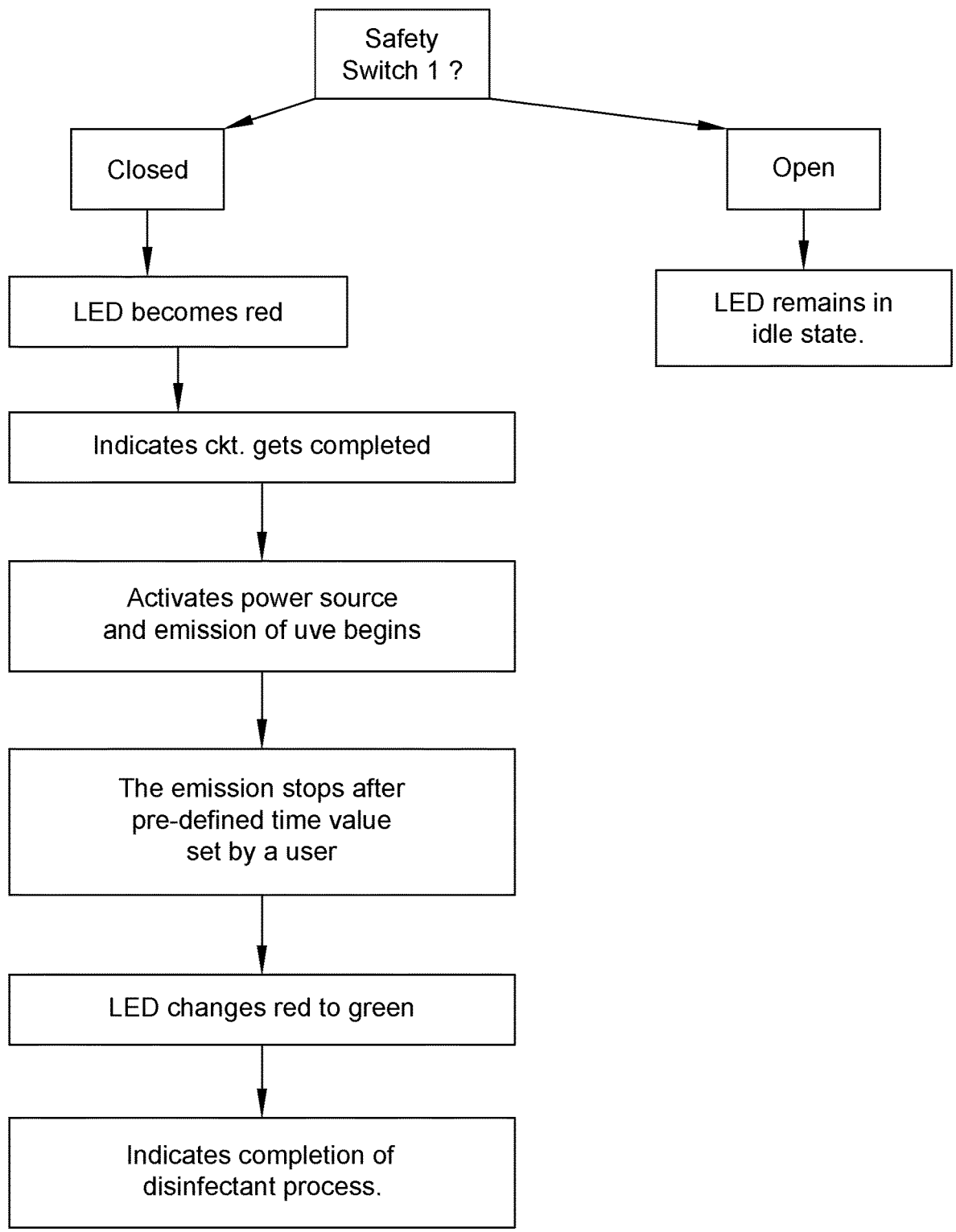

Referring particularly to the drawing for illustration only and not limitation, there is illustrated:

FIG. 1 shows the assembly of aircraft tray table sanitizer fixed behind the airplane seat to sanitize a tray table in accordance with an illustrative embodiment;

FIG. 2 shows the assembly of aircraft tray table sanitizer fixed behind the airplane seat to sanitize a tray table in accordance with an illustrative embodiment;

FIG. 3 shows the assembly of the aircraft tray table when the safety switch is closed; and FIG. 4 shows a process for disinfecting a tray table of the aircraft in the form of a flowchart in accordance with an illustrative embodiment.

DETAILED DESCRIPTION OF DRAWINGS

The foregoing summary, as well as the following detailed description of certain embodiments, will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

One embodiment is illustrated in the figure in The disinfectant tray table contains two components: a tray table 11, and laminar surface 12; which are folded to allow for the sequential unfolding of the two components and placement by the user.

According to the embodiment of the present invention when installed at the backside of the airplane seat 10. When tray table 11 is closed by a user, it faces laminar surface 12 which has the UV light source which may include one or more light-emitting diodes (LEDs) 13 that is configured to emit ultraviolet light. The UVC light LED 13 is turned on and cleans the tray table 11 of any bacteria, viruses, etc. UVC light may have some adverse effect on human skin and vision, to prevent UVC light from touching the skin or eyes of passengers, the edge of said laminar surface 12 is lined with light sealant 21 made of suitable materials which serve as a means of preventing UVC light from leaking while the LEDs 13 are switched on. The disinfectant unit may be a UVC power source that includes one or more processors, one or more timers that are configured to control the operation of the disinfectant unit.

Further, as an additional safety measure, to make sure that UVC LEDs 13 does do not start emission unless the tray tables 11 is closed, i.e.—and switch on the LEDs 13 only when the circuit is completed after safety switch-115 connects with safety switch-116. The LED 13 emit UV light at one or more wavelengths to kill microorganisms. For example, the UV light source LED 13 may emit short-wavelength UV radiation that destroys nucleic acids in various microorganisms, leaving them unable to perform cellular functions. In general, the UV light source LED 13 is configured to emit UV light that kills microorganisms, including pathogens. There is LED 24 which becomes red only when tray table 11 is closed i.e. circuit is completed.

In an embodiment, the system further comprises an alarming unit. The alarming unit (not shown) may be an integrated part of the system which generates an alarm in case of any fault detections. The fault detection may be a failure in circuit closure, a system failure, a presence of a moving object on the tray table, a plastic component.

Furthermore, the in-plane unit may comprise a console for an integrated view of the disinfectant process, to carry out other in-flight operations, which may have a dependency on the tray disinfectant process.

Furthermore, the laminar surface 12 is connected to the back of airplane seat 10 using nut-bolt mechanism 14 which serves as a means of attaching the said laminar surface 12 to the airplane seat 10. The UVC LEDs 13 is powered by removable and rechargeable batteries 18. The batteries are removable because the airline may remove discharge batteries and replace them with charged batteries without hindering the flight schedule or keeping the plane on the ground waiting for the batteries to be charged.

FIG. 1 shows the assembly of aircraft tray table sanitizer fixed behind the airplane seat to sanitize a tray table in accordance with an illustrative embodiment, wherein aircraft tray table sanitizer of the present invention is installed at the backside of the airplane seat 10. In the first embodiment the installed assembly of aircraft tray table sanitizer, wherein the shape and size of the laminar surface 12 is the same as that of the tray table 11. The laminar surface 12 has a plurality of ultraviolet-C(UVC) emitting light-emitting diodes 13 (LED), wherein an edge of laminar surface 12 has a light sealant 12A. The laminar surface 12 is connected to the backside of the airplane seat using a nut-bolt mechanism 14. The assembly includes a latch 15 and a latch 16 to close and lock the tray table 11, wherein the closed position of the latch 15 and the latch 16 works as a safety switch 1. Further, the assembly includes one or more safety switches 17 at different places on the laminar surface 12. In the present embodiment, there is rechargeable and removable power source.

FIG. 2 shows the present invention installed on the backside of the airplane seat which has foldable tray table 19, wherein the table can be folded across the hinge 20. The edges of both halves of the tray table have a light sealant of 21 running over the edges. There is a plurality of UVC emitting LEDs 22 embedded in the sealant rubber tape facing parallel to the surface of the tea table 19. There is also an internal timer (not shown in the figure) that controls the UVC LED light source and switches it off once the tray table is disinfected after a duration ranging from 18 seconds to 30 seconds.

FIG. 3 shows the present invention installed on the backside of airplane seat 10 in which the latches 15 and 16 get closed and locked the tray table 11 which works as a safety switch 1. When the safety switches 1 get closed the circuit gets completed the LED 24 gets switched on, then the microprocessor present in the embodiment activates the power source 18. The activation of the power source results in the emission of UVC radiations from the LED 13 embedded on the laminar surface 12. The Timer present in the embodiments gets activated for a period of 18-30 sec. The color of the LED gets changed from red to green after the emission gets completed.

In a further embodiment, after the system gets deactivated upon completion of predetermined time interval, a rescan process is performed to reconfirm that the tray of each seat may have disinfected properly. In this case also, in case of any detection of viruses, the process may be carried again for another predetermined time interval, which might be for a shorter duration as compared to the first pre-determined interval.

For example, in any of the embodiments described herein, the disinfection light(s) can operate within a variety of treatment wavelengths. At disinfection wavelengths, the light may function to disinfect between 240 nm to about 285 nm in wavelength. In this example, a single light may be tunable between various wavelengths. A controller may be provided that will control the wavelength emitted by the LED. In another example, it may be possible to provide a cluster of disinfection LEDs that are tunable. For example, a first LED set may be tunable to a first wavelength. A second LED set may be tunable to a second wavelength at an instance when the system is operated again for the second time for a pre-determined time interval. Both the first and second LED's may be positioned on one surface, such that the one surface can emit varying wavelengths of light. Although two sets or clusters of LED's are described, there may be more than two clusters or sets of LED. For instance, there may be 3-5 LEDs at different wavelengths so that varying wavelengths could be selected/alternated based on usage or needs.

According to an embodiment of the present invention, as shown in FIG. 3, shows the seatback portion of seat 10 is folded along the surface of the tray table 11. The length of the laminar surface 12 is similar to the length of the existing tray table 10. The Laminar surface 12 is coated with light sealant material over the edges so that the UVC generated from laminar surface 12 does not escape out.

FIG. 4 shows a process for disinfecting a tray table of the aircraft in the form of a flowchart in accordance with an illustrative embodiment, wherein at first, the system determines the activity and inactivity of the safety switch 1. When the latches 15 and 16 get closed a safety switch 1 comes into active mode i.e. the tray table 11 is in close and locks contact with the laminar surface 12 held by nut bolt mechanism 14. In a case, when the latches 15 and 16 are locked the LED 24 becomes red, wherein the red color of the LED indicates the completion of the circuit. The blinking of LED 24 activates the power source 18 which indicates the starting of the emission of UVC light from the LED 13 embedded on the laminar surface 12. Further, the UVC light gets emitted and the disinfectant process begins automatically. After a pre-defined period as set by the user, the LED 24 present in the system automatically changes from red to green which indicates the completion of the disinfectant process. Safety switches 1 remains inactive when latches 15 and 16 do not get locked and the LED 24 will remain in an idle state.

Various implementations of the systems and techniques described here can be realized in digital electronic circuitry, integrated circuitry, specially designed ASICs (application-specific integrated circuits), computer hardware, firmware, software, and/or combinations thereof. These various implementations can include implementation in one or more computer programs that are executable and/or interpretable on a programmable system including at least one programmable processor, which may be special or general-purpose, coupled to receive data and instructions from and to transmit data and instructions to, a storage system, at least one input device, and at least one output device.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

Various embodiments of the invention have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices, or arrangements of devices that are capable of implementing the steps that constitute the method of the disclosure.

The computer system comprises a computer, an input device, a display unit, and the Internet. The computer further comprises a microprocessor. The microprocessor is connected to a communication bus. The computer also includes a memory. The memory may be Random Access Memory (RAM) or Read-Only Memory (ROM). The computer system further comprises a storage device, which may be a hard-disk drive or a removable storage drive, such as, a floppy disk drive, optical disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as the reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

To process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described can also be implemented using only software programming or using only hardware or by a varying combination of the two techniques. The disclosure is independent of the programming language and the operating system used in the computers. The instructions for the disclosure can be written in all programming languages including, but not limited to, "C," "C++," "Visual C++," Java, and "Visual Basic." Further, the software may be in the form of a collection of separate programs, a program module containing a larger program, or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, "Unix," "DOS," "Android," "Symbian," and "Linux."

The programmable instructions can be stored and transmitted on a computer-readable medium. The disclosure can also be embodied in a computer program product comprising a computer-readable medium, or with any product capable of implementing the above methods and systems, or the numerous possible variations thereof.

A person having ordinary skills in the art will appreciate that the system, modules, and sub-modules have been illustrated and explained to serve as examples and should not be considered limiting in any manner. It will be further appreciated that the variants of the above-disclosed system elements, or modules and other features and functions, or alternatives thereof, may be combined to create other different systems or applications.

Although a few implementations have been described in detail above, other modifications are possible. Moreover, other mechanisms for performing the systems and methods described in this document may be used. In addition, the logic flows depicted in the figures may not require the particular order shown, or sequential order, to achieve desirable results. Other steps may be provided, or steps may be eliminated, from the described flows, and other components may be added to, or removed from, the described systems. Accordingly, other implementations are within the scope of the following claims.

DRAWINGS—REFERENCE NUMERALS

10 The backside of an airplane seat
11 Tray table of an airplane seat
12 A laminar surface which has an Ultraviolet light source
12A light sealant
13 Ultraviolet light source
14 Nut bolt/Connection mechanism
15 Safety switch 1
16 Safety switch 1
17 Safety switch 2
18 Removable/Rechargeable power source
19 Foldable tray table of an airplane seat
20 Folding Hinge
21 Light sealants
22 Ultraviolet light source embedded in sealants
24 LED source

What is claimed is:
1. An automated aircraft tray table disinfecting system, comprising;

a tray table including a laminar surface;
a sanitation assembly coupled to the tray table, wherein the sanitation assembly includes:
- one or more (ultraviolet-C) UVC light sources embedded on the laminar surface, wherein the UVC light configure to emit UVC light on the laminar surface of the tray table;
- a light sealant running at an edge of the laminar surface;
- a safety switch configured to one of activate or deactivate the disinfection system, wherein the safety switch operatively coupled to the UVC light sources, wherein the one or more laminar surfaces of the tray table are configured to reflect the UVC light emitted from the UVC light source onto surfaces of the tray table, wherein the switching mechanism of the safety switch is based on a plurality of latches in a lock or unlock position.

2. The system of claim 1, wherein the UVC light source is powered by rechargeable and removable battery, Universal Serial Bus (USB) cable, or by drawing power from the disinfecting system.

3. The system of claim 1, wherein the activation system activates the disinfection system in response to a determination that a set of criteria has been met, and wherein the set of criteria at least includes the tray table is secured in an upright position when the safety switch is closed.

4. The system of claim 3, the safety switch operates when a first latch and a second latch of the plurality of latches are in a closed position.

5. The system of claim 1, wherein the one or more UVC light sources are embedded into light sealant running along the edge of the tray table.

6. The system of claim 1, wherein the disinfecting system is further configured to generate an alarm upon identification of pre-defined one or more conditions.

7. The system of claim 1, wherein the system automatically switches off the UVC LED light source after disinfecting the tray table.

8. The apparatus of claim 1, wherein a controller deactivates the disinfection system to place the disinfection system in an inactive mode after completion of a disinfection process.

* * * * *